United States Patent [19]

Abbott

[11] Patent Number: 5,292,986
[45] Date of Patent: Mar. 8, 1994

[54] ISOPARAFFIN-OLEFIN ALKYLATION CATALYST COMPOSITION AND PROCESS

[75] Inventor: Ronald G. Abbott, Bartlesville, Okla.

[73] Assignee: Phillips Petroleum Company, Bartlesville, Okla.

[21] Appl. No.: 870,983

[22] Filed: Apr. 20, 1992

[51] Int. Cl.$^5$ .................................. C07C 2/62
[52] U.S. Cl. ........................ 585/730; 502/168; 502/150; 502/169; 585/709; 585/724
[58] Field of Search ........... 565/709; 585/709, 724, 585/730; 502/168, 150

[56] References Cited

U.S. PATENT DOCUMENTS

| | | | |
|---|---|---|---|
| 3,708,553 | 1/1973 | Olah | 260/683.47 |
| 3,887,635 | 6/1975 | Parker et al. | 260/683.47 |
| 4,058,575 | 11/1977 | Cahn et al. | 260/666 P |
| 4,069,268 | 1/1978 | Siskin et al. | 585/747 |
| 4,133,841 | 1/1979 | Cosyns et al. | 208/950 |
| 4,587,346 | 5/1986 | Winter et al. | 548/260 |
| 4,677,090 | 6/1987 | Fracasiu | 585/470 |

*Primary Examiner*—Asok Pal
*Attorney, Agent, or Firm*—Charles W. Stewart

[57] ABSTRACT

A novel alkylation catalyst is described which is used in processes for alkylating olefin hydrocarbons with isoparaffin hydrocarbons to produce high octane alkylate products suitable for use as a blending component of gasoline motor fuel. The novel catalyst comprises a mixture of a Lewis acid, a strong Bronsted acid, and a predominant amount of a weaker acid. The novel alkylation catalyst is utilized in a novel process for alkylating olefin hydrocarbons with isoparaffin hydrocarbons. Specifically the novel catalyst comprises antimony pentaflouride, trifluoromethanesulfonic acid and a predominant amount of methanesulfonic acid.

8 Claims, No Drawings

ISOPARAFFIN-OLEFIN ALKYLATION CATALYST COMPOSITION AND PROCESS

The present invention relates to a hydrocarbon conversion process and a catalyst composition to be utilized in said hydrocarbon conversion process. More particularly, the invention relates to an improved alkylation process for the production of an alkylate product by contacting hydrocarbon with a novel catalyst composition.

The use of catalytic alkylation processes to produce branched hydrocarbons having properties that are suitable for use as gasoline blending components is well known in the art. Generally, the alkylation of olefins by saturated hydrocarbons, such as isoparaffins, is accomplished by contacting the reactants with an acid catalyst to form a reaction mixture, settling said mixture to separate the catalyst from the hydrocarbons, and further separating the hydrocarbons, for example, by fractionation, to recover the alkylation reaction product. Normally, the alkylation reaction product is referred to as "alkylate", and it preferably contains hydrocarbons having seven to nine carbon atoms. In order to have the highest quality gasoline blending stock, it is preferred that the hydrocarbons formed in the alkylation process be highly branched.

One of the more desirable alkylation catalysts is hydrofluoric acid, however, the use of hydrofluoric acid as an alkylation catalyst has certain drawbacks. One of the primary problems with the use of hydrofluoric acid as an alkylation catalyst is that it is a highly corrosive substance and is toxic to human beings. The toxicity of hydrofluoric acid to human beings is further complicated by the fact that anhydrous hydrofluoric acid is typically a gas at normal environmental conditions of one atmosphere of pressure and 70° F. The high vapor pressure of hydrofluoric acid can create certain safety concerns in its use as an alkylation catalyst. These safety concerns are created by the ease at which hydrofluoric acid is vaporized and released into the atmosphere, such as in situations where there is an accidental release of a hydrofluoric acid catalyst from its process containment vessels.

In spite of the potential problems with human toxicity and the corrosive characteristics of hydrofluoric acid, industry has in the past determined that the benefits from the use of hydrofluoric acid as an alkylation catalyst outweigh the potential problems. For instance, hydrofluoric acid is an extremely effective alkylation catalyst in that it permits the reaction of olefins by isoparaffins at low process pressures and process temperatures. HF is particularly suited for use as a catalyst in the alkylation of butylenes and, in the case of the alkylation of propylene and amylenes, HF has been used as an effective catalyst whereas other alkylation catalysts, such as sulfuric acid, have been found to be ineffective in such alkylation services. Additionally, the alkylate formed from a hydrofluoric acid alkylation process is of a very high quality having such desirable properties as being a mixture of highly branched compounds that provide a high octane motor fuel. It would be desirable, however, to use an alkylation catalyst that has the desirable features of hydrofluoric acid catalyst but without the negative properties of high vapor pressure and toxicity.

It is, therefore, an object of this invention to provide a novel alkylation catalyst having the desirable properties of providing a high quality alkylate reaction product when utilized in the alkylation of olefins with paraffins but having a low vapor pressure and potentially lower toxicity to humans.

A further object of this invention is to provide a process for the alkylation of olefins with paraffins in the presence of an alkylation catalyst having the desirable properties of low vapor pressure and low human toxicity to produce a high quality alkylate product.

Thus, the process of the present invention relates to the alkylation of a hydrocarbon mixture comprising isoparaffins and olefins by contacting such hydrocarbon mixture with a catalyst comprising: a Lewis acid of the formula $MX_n$, wherein H is selected from the group consisting of Group 4, Group 5, Group 6, Group 13, and Group 15 elements of the Periodic Table, X is a halogen, and n is an integer from 3 to 6; a strong Bronsted acid selected from the group consisting of compounds having the formulas $CX_3SO_3X$, $XSO_3H$, $HX$, $H_2SO_4$ and mixtures thereof, wherein C is carbon, X is a halogen, S is sulfur, O is oxygen, and H is hydrogen; and a predominant amount of a weaker acid of the formula $RSO_3H$, wherein R is an alkyl group, S is sulfur, O is oxygen, and H is hydrogen.

In another aspect of the invention, a novel catalyst composition, having a low vapor pressure and suitable for use in the alkylation of olefin compounds by isoparaffin compounds is provided, which comprises: a Lewis acid of the formula $MX_n$, wherein M is selected from the group consisting of Group 4, Group 5, Group 6, Group 13 and Group 15 elements of the Periodic Table, X is a halogen, and n is an integer from 3 to 6; a strong Bronsted acid selected from the group consisting of compounds having the formulas $CX_3SO_3X$, $XSO_3H$, $HX$, $H_2SO_4$ and mixtures thereof, wherein C is carbon, X is a halogen, S is sulfur, O is oxygen, and H is hydrogen; and a predominant amount of a weaker acid of the formula $RSO_3H$, wherein R is an alkyl group, S is sulfur, O is oxygen, and H is hydrogen.

Other objects and advantages of the invention will be apparent from the foregoing description of the invention and the appended claims as well as from the detailed description of the invention which follows.

The novel composition of the present invention is suitable for use as an alkylation catalyst and can comprise, consist of, or consist essentially of a Lewis acid, a strong Bronsted and a predominant amount of a weaker acid.

The Lewis acid component of the composition will generally be of the chemical formula $MX_n$, where M is selected from the group consisting of Group 4, Group 5, Group 6, Group 13 and Group 15 elements of the Periodic Table, X is a halogen, and n is an integer from 3 to 6. Among the metal halides which constitute the Lewis acid component of the composition, it is preferred that the metal halide be selected from the group consisting of antimony pentafluoride, tantalum pentafluoride, niobium pentafluoride, vanadium pentafluoride, tungsten hexafluoride, titanium tetrafluoride, molybdenum hexafluoride, boron trifluoride, aluminum trifluoride, bismuth pentafluoride, arsenic pentafluoride, and mixtures of two or more thereof. The most preferred metal halide constituent of the composition is antimony pentafluoride.

When referring herein to group numbers of the periodic table, the nomenclature used is that adopted by the American Chemical Society Committee on Nomenclature on Nov. 14, 1983 and as published in the *Journal of*

*Chemical Education*, vol. 61, number 2, page 136 (1984). Under this nomenclature and as used herein: Group 4 elements consist of titanium (Ti), zirconium (Zr), and hafnium (Hf); Group 5 elements consist of vanadium (V), niobium (Nb), tantalum (Ta); Group 6 elements consist of chromium (Cr), molybdenum (Mo), tungsten (W); Group 13 elements consist of boron (B), aluminum (Al), gallium (Ga), indium (In), and thallium (Tl); and Group 15 elements consist of nitrogen (N), phosphorus (P), arsenic (As), antimony (Sb) and bismuth (Bi).

The strong Bronsted acid component of the composition will generally be a strong acid compound such as halosulfuric acid ($XSO_3H$, where X is a halogen), trihalomethanesulfuric acid ($CX_3SO_3H$), hydrogen halide (HX), sulfuric acid ($H_2SO_4$) or mixtures of two or more thereof. It is preferred for the halogen of said strong acid compound to be fluorine. Most preferably, however, the strong Bronsted acid component is trifluoromethane sulfonic acid.

The weaker acid component of the composition will generally be an alkyl sulfonic acid compound of the formula $RSO_3H$, where R is an alkyl group, S is sulfur, O is oxygen, and H is hydrogen. The preferred alkyl sulfonic acid compound of the composition is methanesulfonic acid.

It has been discovered that, contrary to some of the teachings of the prior art, mixtures of certain Lewis acids and strong Bronsted acids fail to provide a catalyst composition that suitably catalyzes the alkylation of olefin hydrocarbons with isoparaffin hydrocarbons. In particular, it has been discovered that mixtures of a single metal halide Lewis acid and a single strong Bronsted acid, such as, for example, trihalomethanesulfuric acid, do not have suitable catalytic properties for catalyzing the alkylation of olefin hydrocarbons with isoparaffin hydrocarbons. More particularly, a mixture of the Lewis acid, antimony pentafluoride, and the Bronsted acid of trifluoromethanesulfonic acid, or triflic acid, has been found to be ineffective as an alkylation catalyst especially when the molar ratio of the Lewis acid to the Bronsted acid is in the range of from 0.25:1 to 3.0:1, or, more specifically, when it is in the range of from 0.5:1 to 1.5:1.

It has further been discovered that large concentrations of a weaker acid can be utilized as a suitable alkylation catalyst, without significant negative consequences upon an alkylate end-product, when the weaker acid is used in combination with a Lewis acid and a strong Bronsted acid. Therefore, this invention contemplates the use of a predominant amount of weaker acid, as described herein, in combination with a Lewis acid and a strong Bronsted acid, as a catalyst system or composition for catalyzing the alkylation of olefin hydrocarbons by isoparaffins. Thus, generally, the weaker acid will be present in the catalyst system or composition in an amount exceeding about 50 mole percent based upon the total moles of the Lewis acid, the strong Bronsted acid and the weaker acid. Preferably, the weaker acid component of the composition will be present in an amount exceeding about 60 mole percent based on the total moles of the composition; and, most preferably, the weaker acid will be present in the composition in the range of from 65 to 75 mole percent based on the total moles of the composition.

In terms of the molar ratio of the weaker acid to the combination of strong Lewis and Bronsted acids, it has been found that it is important to the utility of the catalyst system when it is used in the production of high quality alkylate for this molar ratio to exceed about 1:1. But, preferably, the molar ratio of the weaker acid to the combination of stronger acids should exceed 1.5:1. And, most preferably, this molar ratio can range from 1.8:1 to 3:1.

The trifluoromethanesulfonic acid component of the novel composition has a chemical formula of $CF_3SO_3H$. Typical commercial grades of trifluoromethanesulfonic acid can be used to formulate the catalyst composition. In general, these commercial grades should have purities of at least 98 weight percent of trifluoromethanesulfonic acid.

The methanesulfonic acid utilized as a component of the novel catalyst composition has the chemical formula of $CH_3SO_3H$. Any suitable commercial grade of methanesulfonic acid can be used to formulate the catalyst composition; but, preferably, the commercial grade of methanesulfonic acid should have a purity of at least 98 weight percent.

Alkylation processes contemplated in the present invention are those liquid phase processes wherein mono-olefin hydrocarbons such as propylene, butylenes, pentylenes, hexylenes, heptylenes, octylenes and the like are alkylated by isoparaffin hydrocarbons such as isobutane, isopentane, isohexane, isoheptane, isooctane and the like for production of high octane alkylate hydrocarbons boiling in the gasoline range and which are suitable for use in gasoline motor fuel. Preferably, isobutane is selected as the isoparaffin reactant and the olefin reactant is selected from propylene, butylenes, pentylenes and mixtures thereof for production of an alkylate hydrocarbon product comprising a major portion of highly branched, high octane value aliphatic hydrocarbons having at least seven carbon atoms and less than ten carbon atoms.

In order to improve selectivity of the alkylation reaction toward the production of the desirable highly branched aliphatic hydrocarbons having seven or more carbon atoms, a substantial stoichiometric excess of isoparaffin hydrocarbon is desirable in the reaction zone. Molar ratios of isoparaffin hydrocarbon to olefin hydrocarbon of from about 2:1 to about 25:1 are contemplated in the present invention. Preferably, the molar ratio of isoparaffin-to-olefin will range from about 5 to about 20; and, most preferably, it shall range from 8.5 to 15.

Isoparaffin and olefin reactant hydrocarbons normally employed in commercial alkylation processes are derived from refinery process streams and usually contain small amounts of impurities such as normal butane, propane, ethane and the like. Such impurities are undesirable in large concentration as they dilute reactants in the reaction zone, thus decreasing reactor capacity available for the desired reactants and interfering with good contact of isoparaffin with olefin reactants. Additionally, in continuous alkylation processes wherein excess isoparaffin hydrocarbon is recovered from an alkylation reaction effluent and recycled for contact with additional olefin hydrocarbon, such nonreactive normal paraffin impurities tend to accumulate in the alkylation system. Consequently, process charge streams and/or recycle streams which contain substantial amounts of normal paraffin impurities are usually fractionated to remove such impurities and maintain their concentration at a low level, preferably less than about 5 volume percent, in the alkylation process.

Alkylation reaction temperatures within the contemplation of the present invention are in the range of from about 0° F. to about 150° F. Lower temperatures favor alkylation reaction of isoparaffin with olefin over competing olefin side reactions such as polymerization. However, overall reaction rates decrease with decreasing temperatures. Temperatures within the given range, and preferably in the range from about 30° F. to about 130° F., provide good selectivity for alkylation of isoparaffin with olefin at commercially attractive reaction rates. Most preferably, however, the alkylation temperature should range from 50° F. to 100° F.

Reaction pressures contemplated in the present invention are sufficient to maintain reactants in the liquid phase and may range from ambient pressure to about fifteen (15) atmospheres of pressure. Reactant hydrocarbons may be normally gaseous at alkylation reaction temperatures, thus reaction pressures in the range of from about 40 pounds gauge pressure per square inch (psig) to about 160 psig are preferred. With all reactants in the liquid phase, increased pressure has no significant effect upon the alkylation reaction.

Generally, the contact time should be sufficient for essentially complete conversion of the olefin reactant in an alkylation zone. Preferably, contact times for hydrocarbon reactants in an alkylation zone, in the presence of the alkylation catalyst of the present invention, can range from about 0.05 minute to about 60 minutes. In the alkylation process of the present invention, employing isoparaffin-to-olefin molar ratios in the range of about 2:1 to about 25:1, wherein the alkylation reaction mixture comprises about 40-90 volume percent acid catalyst phase and about 60-10 volume percent hydrocarbon phase, and wherein good contact of olefin with isoparaffin is maintained in the reaction zone, essentially complete conversion of olefin may be obtained at olefin space velocities in the range of about 0.1 to about 200 volumes olefin per hour per volume catalyst (v/v/hr.). Optimum space velocities will depend upon the type of isoparaffin and olefin reactants utilized, the particular compositions of alkylation catalyst, and the alkylation reaction conditions. Consequently, the preferred contact times are sufficient for providing an olefin space velocity in the range of about 0.1 to about 200 (v/v/hr.) and allowing essentially complete conversion of olefin reactant in the alkylation zone.

The process may be carried out either as a batch or continuous type of operation, although it is preferred for economic reasons to carry out the process continuously. It has been generally established that in alkylation processes, the more intimate the contact between the feedstock and the catalyst the better the quality of alkylate product obtained. With this in mind, the present process, when operated as a batch operation, is characterized by the use of vigorous mechanical stirring or shaking of the reactants and catalyst.

In continuous operations, in one embodiment, reactants may be maintained at sufficient pressures and temperatures to maintain them substantially in the liquid phase and then continuously forced through dispersion devices into the reaction zone. The dispersion devices may be jets, nozzles, porous thimbles and the like. The reactants are subsequently mixed with the catalyst by conventional mixing means such as mechanical agitators or turbulence of the flow system. After a sufficient time, the product can then be continuously separated from the catalyst and withdrawn from the reaction system while the partially spent catalyst is recycled to the reactor. If desired, a portion of the catalyst can be continuously regenerated or reactivated by any suitable treatment and returned to the alkylation reactor.

The following examples demonstrate the advantages of the present invention. These examples are by way of illustration only, and are not intended as limitations upon the invention as set out in the appended claims.

EXAMPLE I

Under a blanket of dry nitrogen, 95.4 g (0.44 moles) $SbF_5$, 66.0 g (0.44 moles) $CF_3SO_3H$ and 42.3 g (0.44 moles) $CH_3SO_3H$ were combined with stirring in a 300 mL monel autoclave and cooled to 60° F. Upon increasing the stirring rate to 2500 rpm, 100 mL of an 8.5:1 isobutane:2-butenes feed was added by nitrogen backpressure into the catalyst mixture at a rate of 25 mL/minute. The mixture was then stirred an additional 5 minutes and cooled to 60° F. under 150 psig nitrogen. The hydrocarbon phase was isolated, neutralized and evaluated by gas chromatography. The test results are presented in Table I.

EXAMPLE II

Approximately 165 g of the catalyst mixture from Example I was isolated and returned to the autoclave; 38.7 g were lost in transfer. An additional 30 g of $CH_3SO_3H$ was added to the catalyst mixture. Assuming essentially equal losses of each catalyst component of the catalyst from Example I, the new catalyst mixture was comprised of approximately 0.36 moles $SbF_5$, 0.36 moles $CF_3SO_3H$ and 0.67 moles of $CH_3SO_3H$.

The alkylation reaction was conducted as in Example I with 100 mL of an 8.5:1 isobutane:2-butenes feed being introduced with stirring into the catalyst at 60° F. under nitrogen backpressure at a feed rate of 25 mL/minute. The mixture was stirred 5 minutes as before, followed by isolation, neutralization and evaluation of the hydrocarbon layer by gas chromatography. The test results are presented in Table I.

EXAMPLE III

An alkylation reaction was conducted in a procedure identical to that of Example I using a catalyst mixture comprised of 51.0 g (0.23 moles) $SbF_5$, 35.7 g (0.24 moles) $CF_3SO_3H$ and 92 g (0.96 moles) $CH_3SO_3H$. The test results are presented in Table I.

EXAMPLE IV

Approximately 143 g of the catalyst mixture from Example I was isolated and returned to the autoclave; 35.7 g were lost in transfer. An additional 14.8 g (0.15 moles) of $CH_3SO_3H$ was added to the catalyst mixture. Assuming essentially equal losses of each catalyst component of the catalyst from Example I, the new catalyst mixture was comprised of approximately 0.19 moles $SbF_5$, 0.19 moles $CF_3SO_3H$ and 0.92 moles of $CH_3SO_3H$.

The alkylation reaction was conducted as in Example I with 100 mL of an 8.5:1 isobutane:2-butenes feed being introduced with stirring into the catalyst at 60° F. under nitrogen backpressure at a feed rate of 25 mL/minute. The mixture was stirred 5 minutes as before, followed by isolation, neutralization and evaluation of the hydrocarbon layer. The test results are presented in Table 1.

EXAMPLE V

An 8.5:1 isobutane:2-butenes feed was reacted using a catalyst mixture comprised of 40 g (0.18 moles) $SbF_5$ and 18 g (0.18 moles) $FSO_3H$ in a procedure identical to that of Example I. The resulting hydrocarbon product was isolated, neutralized and evaluated by gas chromatography. The test results are presented in Table I.

TABLE I

Alkylate from Reactions Utilizing Various Catalyst Compositions

| Catalyst (Molar Ratio) | 1:1:0 SbF$_5$:FSO$_3$H | 1:1:1 SbF$_5$:CF$_3$SO$_3$H: CH$_3$SO$_3$H | 1:1:2 SbF$_5$:CF$_3$SO$_3$H: CH$_3$SO$_3$H | 1:1:4 SbF$_5$:CF$_3$SO$_3$H: CH$_3$SO$_3$H | 1:1:5 SbF$_5$:CF$_3$SO$_3$H: CH$_3$SO$_3$H |
|---|---|---|---|---|---|
| Wt. % n-C$_4$ | 35.0 | 33.0 | 21.5 | 4.1 | 1.4 |
| Wt. % TMP* | 1.4 | 1.1 | 4.3 | 51.4 | 52.0 |
| Wt. Ratio TMP:DMH* | 0.1 | 0.2 | 0.33 | 3.3 | 3.5 |
| Wt. % C$_8$ | 14.8 | 9.4 | 17.3 | 68.2 | 68.3 |
| Wt. % C$_9$+ | 6.4 | 8.6 | 10.5 | 9.9 | 14.3 |

*TMP = trimethylpentanes; DMH = dimethylhexanes

While this invention has been described in terms of the presently preferred embodiment, reasonable variations and modifications are possible by those skilled in the art. Such variations and modifications are within the scope of the described invention and the appended claims.

That which is claimed is:

1. A composition comprising antimony pentafluoride, trifluoromethanesulfonic acid, and a predominant amount of methanesulfonic acid.

2. A composition as recited in claim 1 wherein the molar ratio of antimony pentafluoride to trifluoromethanesulfonic acid is in the range of from about 0.5:1 to 1.5:1 and said predominant amount of methanesulfonic acid is such that methanesulfonic acid is present in said composition in an amount exceeding 60 mole percent.

3. A process comprising contacting a hydrocarbon mixture comprising isoparaffins and olefins with a catalyst comprising antimony pentafluoride, trifluoromethanesulfonic acid, and a predominant amount of methanesulfonic acid.

4. A process as recited in claim 3 wherein the molar ratio of antimony pentafluoride to trifluoromethanesulfonic acid is in the range of from about 0.5:1 to 1.5:1 and said predominant amount of methanesulfonic acid is such that it is present in said composition in an amount exceeding 60 mole percent.

5. A composition comprising
   antimony pentafluoride;
   trifluoromethane sulfonic acid; and
   methanesulfonic acid,
   whereas the molar ratio of antimony pentafluoride to trifluoromethane sulfonic acid in said composition is in the range of from about 0.25:1 to 3:1, and wherein the methanesulfonic acid is present in said composition in an amount exceeding about 50 mole percent.

6. A composition as recited in claim 5 wherein the molar ratio of antimony pentafluoride to trifluoromethane sulfonic acid is in the range of from about 0.5:1 to 1.5:1 and wherein the methanesulfonic acid is present in said composition in an amount exceeding 60 mole percent.

7. A process comprising contacting a hydrocarbon mixture comprising isoparaffin and olefins with a catalyst comprising:
   antimony pentafluoride;
   trifluoromethane sulfonic acid; and
   methanesulfonic acid,
   whereas the molar ratio of antimony pentafluoride to trifluoromethane sulfonic acid in said composition is in the range of from about 0.25:1 to 3:1, and wherein the methanesulfonic acid is present in said composition in an amount exceeding about 50 mole percent.

8. A process as recited in claim 7 wherein the molar ratio of antimony pentafluoride to trifluoromethane sulfonic acid is in the range of from about 0.5:1 to 1.5:1 and wherein the methanesulfonic acid is present in said composition in an amount exceeding 60 mole percent.

* * * * *